United States Patent [19]
Bryant et al.

[11] Patent Number: 5,209,740
[45] Date of Patent: May 11, 1993

[54] CATHETER ADAPTER HAVING RETENTION NOTCHES

[75] Inventors: Peter L. Bryant, Libertyville; Nicolaos A. Drivas, Des Plaines, both of Ill.

[73] Assignee: Abbott Laboratories, Abbott Park, Ill.

[21] Appl. No.: 796,149

[22] Filed: Nov. 22, 1991

[51] Int. Cl.⁵ ............................................. A61M 25/00
[52] U.S. Cl. ................................... 604/243; 604/283
[58] Field of Search ............... 604/164, 180, 240–243, 604/283, 905; 285/81, 334.3, 343, 339, 353

[56] References Cited
U.S. PATENT DOCUMENTS

| | | | |
|---|---|---|---|
| 4,419,094 | 12/1983 | Patel | 604/165 |
| 4,886,507 | 12/1989 | Patton et al. | 604/284 |
| 5,053,015 | 10/1991 | Gross | 604/243 |

*Primary Examiner*—John D. Yasko
*Assistant Examiner*—Anthony Gutowski
*Attorney, Agent, or Firm*—Thomas M. Breininger

[57] ABSTRACT

A catheter adapter of the type wherein compression applied to the catheter provides a retention force thereon and wherein notches are provided on the adapter for wrapping the catheter around the adapter in a manner such that a force applied to the catheter does not constitute a catheter separating force.

4 Claims, 2 Drawing Sheets

CATHETER ADAPTER HAVING RETENTION NOTCHES

BACKGROUND OF THE INVENTION

A commonly used adapter for field-connection to catheters is an adapter which includes a cup-shaped female member having an internal thread, an externally threaded male member for threaded engagement with the cup-shaped member which is characterized by an axially bored nose portion, and an axially bored resilient grommet disposed therebetween. The end of a catheter is inserted into the nose portion of the male member and into the grommet when the two threaded members are in a loosened mode. When the male member is threadedly tightened into the cup-shaped member, the configuration thereof and that of the grommet are such that the grommet is compressed onto the portion of the catheter extending therethrough to provide a retention force on the catheter. Finger-engageable members may be provided on the sides of the nose portion of the male member to facilitate tightening same into the cup-shaped member. One problem is occlusion of the catheter if the compression forces thereon are too great. The smaller the diameter of the catheter the greater is this danger of occlusion so it is a particular problem with the relatively tiny spinal catheters wherein the outer diameter may be in the order of only 0.010–0.015 inches.

So it is most difficult to tighten the threaded members of such an adapter sufficiently to provide a suitable retention force against an axial force applied to a catheter, particularly one of the smaller ones, without occluding the catheter. Either occlusion of the catheter or separation of same from the adapter could be critical as to the welfare of a patient.

SUMMARY OF THE INVENTION

This problem has been solved by the present invention which comprises an improvement to such catheters whereby a force applied to the catheter does not result in a direct force tending to separate the catheter from the adapter. By notching the finger-engageable wings on the nose portion of the male member in a manner such that the catheter, as it exits the nose portion, may be passed through the notched wing members and wrapped one or more times around the body of the male member, any force applied to the catheter merely tightens its wrap around the male member rather than exerting a separation force on the catheter. With this new and novel improvement, the compression force on the catheter may be lessened to insure against occlusion of same.

An object of the present invention is to provide a new and novel catheter adapter which has improved catheter retention force characteristics.

Another object of the present invention is to provide a new and novel catheter having notched members which facilitate wrapping the catheter around the adapter in a manner such that any force applied to the catheter is not seen as a force tending to separate the catheter from the adapter.

BRIEF DESCRIPTION OF THE DRAWINGS

The features which are believed to characterize this invention are set forth in the appended claims. The invention itself, together with its features, objects, and attendant advantages, will be best understood by reference to the following detailed description of a presently preferred embodiment thereof, taken in conjunction with the accompanying drawings, in which:

DESCRIPTION OF THE PREFERRED EMBODIMENT

Figure 1:
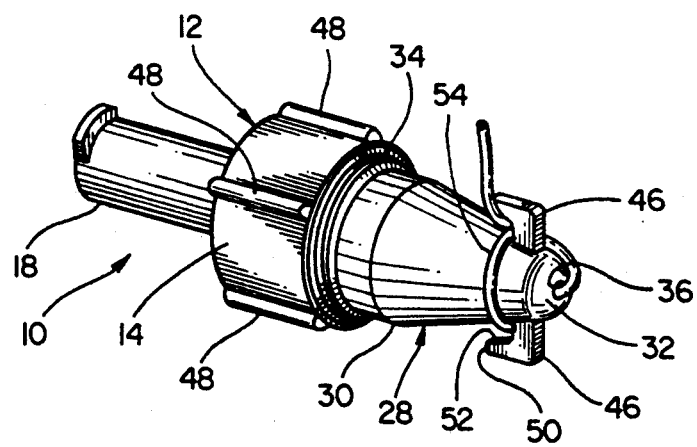
FIG. 1 is a perspective view of a preferred embodiment of a catheter adapter of the present invention.
Figure 2:
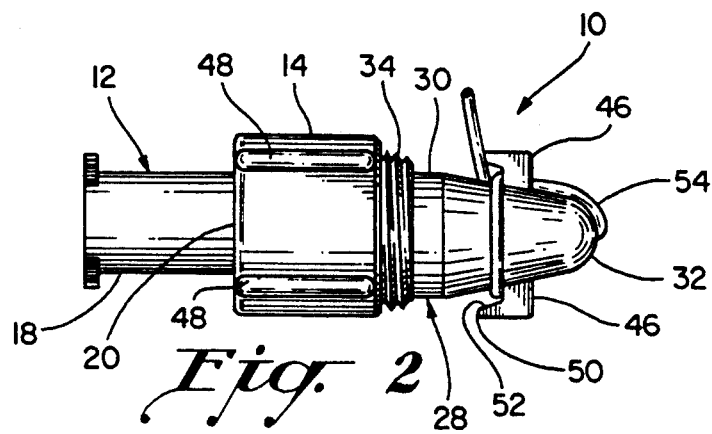
FIG. 2 is a side elevational view thereof.
Figure 4:
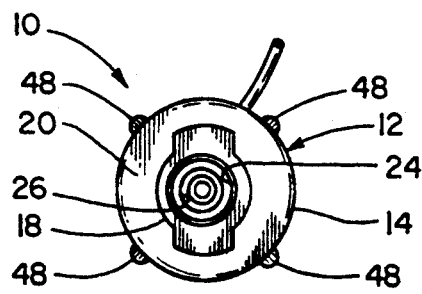
FIG. 4 is a left end elevational view thereof.
Figure 3:
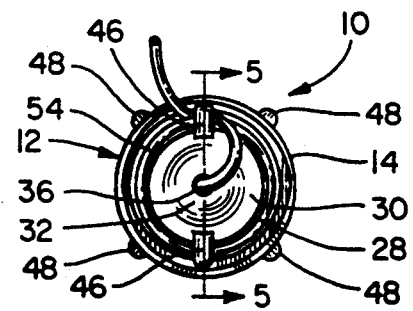
FIG. 3 is a right end elevational view thereof.
Figure 5:
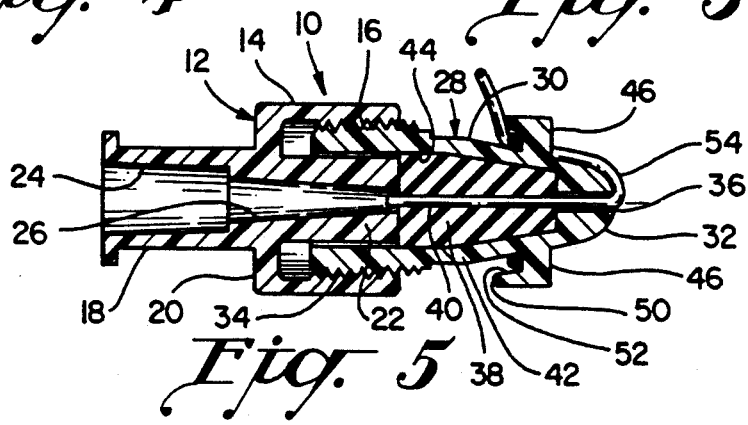
FIG. 5 is a longitudinal sectional view taken generally along line 5—5 of FIG. 3.

Referring now to the drawings, an adapter 10 embodying the invention includes, as best shown in FIG. 5, a female member 12 which is characterized by a cup-shaped portion 14 having an internal thread 16, by an axially bored stem portion 18 which extends away from a base 20 of the cup-shaped portion 14, and by a concentric hub portion 22 which extends from the base 20 into the cup-shaped portion 14. The stem portion 18 is provided with a Luer taper 24 for receiving a known type tubing connector (not shown), which taper 24 opens into a conically shaped bore 26 which extends through the hub portion 22.

The adapter also includes a male member 28 which is characterized by a sleeve portion 30 having one end substantially closed by a nose portion 32. The opposite end of the sleeve portion 30 fits over the hub portion 22 of the female member 12 and has an external thread 34 in threaded engagement with the internal thread 16 of the female member 12. An axial bore 36 extends through the nose portion 32.

Disposed within the sleeve portion 30 is an axially bored grommet 38 formed of resilient material and having an axial bore 40 extending therethrough. One end of the grommet 38 abuts against the end of hub portion 22 and the other end abuts against the inner surface of the nose portion 32. The nose-end of the grommet 38 is provided with a conical surface 42 which is in engagement with a mating conical surface 44 on the inner surface of the sleeve portion 30 of the male member 28 for a purpose which will be discussed hereinafter.

A pair of diametrically opposite, radially and longitudinally disposed wings 46 are provided on the outer surface of the sleeve portion 30 of the male member 28 to facilitate rotatably tightening the male member 28 into the female member 12. The outer surface of the cup-shaped portion 14 of the female member 12 is provided with longitudinally disposed rib formations 48 to facilitate gripping of same. Edges 50 of the wings 46 which face away from the nose portion 32 and toward the female member 12 are provided with notches 52 for a purpose which will be made clear hereinafter.

In field assembling the adapter 10 to the proximal end of a catheter 54, such as a very tiny spinal catheter having an outer diameter of from 0.010–0.015 inches, the male member 28 is first loosened relative to the female member 12 to relieve any compression force on the grommet 38. The proximal end of the catheter 54 may then be inserted through the axial bore 36 in the nose portion 32 of the male member 28 and into the axial bore 40 in the grommet 38. The male member 28 is then carefully tightened into the female member 12 whereby, due to the mating conical surfaces 42 and 44 on the grommet 38 and sleeve portion 30 of the male member 28, respectively, the resilient grommet 38 is compressed about the length of the catheter 54 disposed in the grommet bore 38 to impose a retention force thereon and thus prevent axial separation of the catheter 54 from the adapter 10.

Particularly with the finer, tiny spinal catheters, care must be used in torquing down the adapter 10 to insure that the catheter is not occluded which would be just as detrimental to a patient as separation of the catheter 54 from the adapter 10.

To improve the retention force on the catheter 54 without increasing the compressive force thereon, the catheter 54 as it leaves the nose portion 32 is directed rearwardly along the outer surface of the sleeve portion 30 and then at a generally right angle into one of the wing notches 52 after which it is wrapped one or more times around the male member 28 in a plane generally normal to the longitudinal axis of the adapter 10. Therefore, any force applied to the catheter 54 is absorbed by frictional and self locking aspects of the wrapped-around catheter 54 whereby substantially no separation force is transmitted to the portion of the catheter 54 disposed in the 10.

Figure 6:
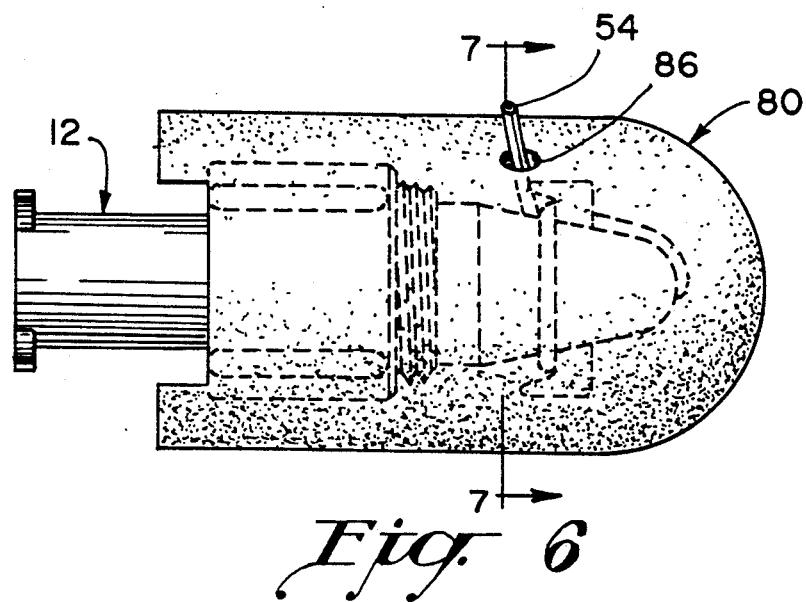
FIG. 6 is a side elevational view similar to FIG. 2 and showing an optional feature which includes a sponge-like retainer.
Figure 7:
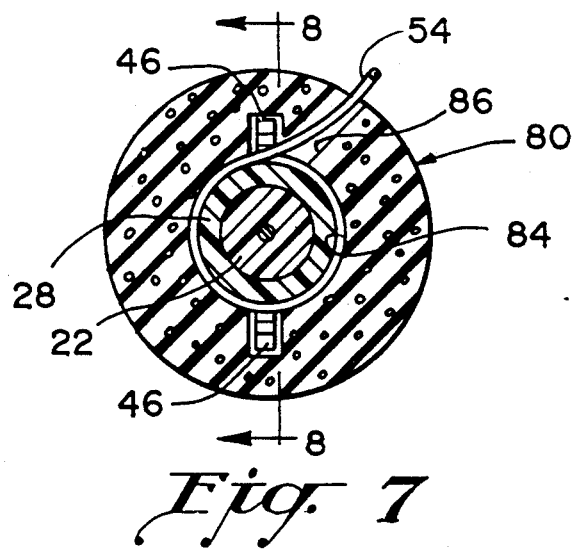
FIG. 7 in a cross-sectional view taken generally long the plane 7—7 in FIG. 6.
Figure 8:
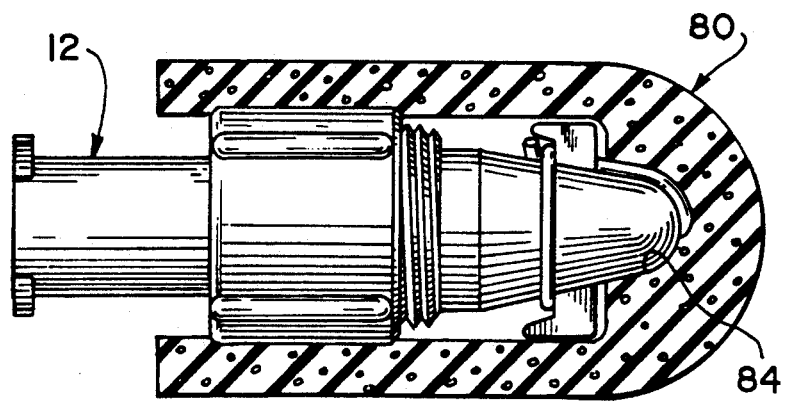
FIG. 8 is a partial cross-sectional view taken generally along the plane 8—8 in FIG. 7 to show the sponge-like member in cross section around the adaptor shown in side elevation.

If desired, a sponge-like retainer 80 (FIGS. 6-8) having an adapter-shaped cavity 84 including a catheter exit-passage 86 may be disposed about the adapter 10 merely to insure frictional contact of the wrapped-around catheter 54 with the outer surface of the male member 28.

The scope of the invention is set forth in the following claims rather than in the foregoing description of the presently preferred embodiment and it will be obvious to those skilled in the art that changes and modifications may be made without departing from the spirit and scope of the invention.

We claim:

1. An improvement in an adapter of the type having an axially bored female housing portion with an internally threaded section, a bored externally threaded male housing portion having a conically tapered inner bore, a bored generally conically shaped resilient grommet disposed against the conically tapered inner bore of the male housing portion and adapted to be squeezed against the outer surface of the end of a catheter inserted into the adapter as the male body portion is threadedly tightened into said female body portion to provide a retention force thereon, and wherein the male body portion is provided with a pair of diametrically opposite radially disposed finger-engageable wing members which serve as an aid in tightening the male body portion into the female body portion, the improvement comprising notch means formed in at least one of said wing members for receiving the catheter after same exits from the end of said male body portion and to facilitate wrapping said catheter about said male housing portion in frictional contact therewith whereby to improve said retention force, wherein said notch means faces in the same direction that said male body portion is tightened.

2. The improvement of claim 1 wherein each of said notches opens toward said female body portion whereby the catheter exiting the end of said male body portion is reversed and then engaged in one of said notches and wrapped around said male body portion in a plane normal to the axis of said adapter to improve the catheter retention characteristics of said adapter.

3. An improvement in an adapter of the type having an axially bored female housing portion with an internally threaded section, a bored externally threaded male housing portion having a conically tapered inner bore, a bored generally conically shaped resilient grommet disposed against the conically tapered inner bore of the male housing portion and adapted to be squeezed against the outer surface of the end of a catheter inserted into the adapter as the male body portion is threadedly tightened into said female body portion to provide a retention force thereon, and wherein the male body portion is provided with a pair of diametrically opposite radially disposed finger-engageable wing members which serve as an aid in tightening the male body portion into the female body portion, the improvement comprising notch means formed in at least one of said wind members for receiving the catheter after same exits from the end of said male body potion and to facilitate wrapping said catheter about said male housing portion in frictional contact therewith whereby to improve said retention force, wherein said notch means comprises a notch formed in each of said wind members adjacent the outer surface of said male body portion.

4. An improvement in an adapter of the type having an axially bored female housing portion with an internally threaded section, a bored externally threaded male housing portion having a conically tapered inner bore, a bored generally conically shaped resilient grommet disposed against the conically tapered inner bore of the male housing portion and adapted to be squeezed against the outer surface of the end of a catheter inserted into the adapter as the male body portion is threadedly tightened into said female body portion to provide a retention force thereon, and wherein the male body portion is provided with a pair of diametrically opposite radially disposed finger-engageable wing members which serve as an aid in tightening the male body portion into the female body portion, the improvement comprising notch means formed in at least one of said wing members for receiving the catheter after same exits from the end of said male body portion and to facilitate wrapping said catheter about said male housing portion in frictional contact therewith whereby to improve said retention force, and a sponge-like retainer having an adapter-shaped cavity including a catheter exit-passage for disposal about said adapter to aid in insuring said frictional contact of said wrapped catheter with said male body portion.

* * * * *